United States Patent [19]

Gabrilove

[11] Patent Number: 4,961,926

[45] Date of Patent: Oct. 9, 1990

[54] METHODS FOR PREVENTION AND TREATMENT OF MUCOSITIS WITH GRANULOCYTE COLONY STIMULATING FACTOR

[75] Inventor: Janice L. Gabrilove, New York, N.Y.

[73] Assignee: Sloan-Kettering Institute For Cancer Research, New York, N.Y.

[21] Appl. No.: 122,784

[22] Filed: Nov. 19, 1987

[51] Int. Cl.$^5$ .................... A61K 37/02; A61M 36/00
[52] U.S. Cl. ................................. 424/85.1; 424/11; 424/9; 514/2; 514/8; 514/21; 514/917; 514/922; 600/1
[58] Field of Search ................ 514/8, 2, 21, 917, 922; 424/85.1, 1.1, 9; 128/1.1, 1 R

[56] References Cited

PUBLICATIONS

Moore et al. *PNAS* 84, 1987, pp. 7134–7138.
Matsumata et al., *Inf and Inn* 55(11) 1987, pp. 2715–2720.
Chirigos et al., "Cancer Detection and Prevention" Suppl 1, 1987, pp. 385–387.
*J. Clin Invest*, Supp; 1987, vol. 79, pp. 1549–1557.
Henderson, Drug and Hemabologic Reacton, Ed Gruve, 1974, pp. 207–221.
Pizzo, P. A. and Young, R. C., "Infections in the Cancer Patient," in *Cancer Principles and Practices of Oncology*, DeVita, et al., Eds., pp. 1963–1998 (1985).
DeVita, V. T., *Journal of Clinical Oncology*, vol. 4, pp. 1157–1159 (1986).
Souza, L. M., et al., *Sciences*, vol. 232, pp. 61–65 (1986).
Welte, K., et al., *Journal of Exp. Medicine*, vol. 165, pp. 941–948 (1987).
Welte, K., et al., *Experimental Hematology* (ISEH), vol. 16, p. 72 (1987).
Sternberg, C. N., et al., *Journal of Urology*, vol. 133, pp. 403–407 (1985).
Blum, R. H., et al., "Principles of Dose, Schedule, and Combination Chemotherapy", in *Cancer Medicine*, Holland J. and Frei, E. III, Eds., Lea and Febiger, Philadelphia, pp. 730–752 (1982).

*Primary Examiner*—Garnette Draper
*Attorney, Agent, or Firm*—John P. White

[57] ABSTRACT

This invention provides method of preventing mucositis in a subject susceptible to mucositis comprising administering to the subject a prophylactically effective amount of granulocyte colony stimulating factor or a polypeptide analog thereof having substantially the same amino acid sequence and the activity of naturally occurring granulocyte colony stimulating factor. This invention further provides a method of treating mucositis in a subject having mucositis comprising administering to the subject a therapeutically effective amount of granulocyte colony stimulating factor or a polypeptide analog thereof having substantially the same amino acid sequence and the activity of naturally occurring granulocyte colony stimulating factor.

20 Claims, 1 Drawing Sheet

METHODS FOR PREVENTION AND TREATMENT OF MUCOSITIS WITH GRANULOCYTE COLONY STIMULATING FACTOR

BACKGROUND OF THE INVENTION

The present disclosure relates to a method for preventing or reducing epithelial cell injury in a patient This epithelial cell injury results in mucositis, in particular stomatitis. In particular, the disclosure relates to a method for relieving oral discomfort and inflammation associated with anti-neoplastic therapy-induced mucositis.

Neutropenia results from anti-neoplastic treatment, in particular chemotherapy is a major factor contributing to infectious morbidity and mortality in cancer patients, Pizzo, et al., "Infections in the cancer patient" In: Cancer Principles and Practice of Oncology (2) and DeVita, et al. eds., 1985; 1963–1998. A reduction in the doses of chemotherapy which should be administered is often necessary due to the myelosuppressive toxicity of many anti-neoplastic agents. The inability to administer full doses of chemotherapy, in turn, is thought to impair (or adversely influence) the anti-tumor response of therapeutic protocols designed to treat cancer, DeVita, "Dose response is alive and well", J Clin Onc, 1986; 4:1157–1159. The ability to either accelerate recovery from or prevent chemotherapy-induced myelosuppression would clearly be of potential benefit. Dose limiting toxicity of anti-tumor agents involves not only deleterious effects on the cells of the bone marrow, but injures rapidly dividing epithelial cells of the oral mucosa and gastrointestinal tract. The compromised mucosa coupled with the myelosuppression effects of chemotherapy predispose patients to oral mucositis and subsequent secondary infection. Chemotherapy-induced stomatitis occurs as a result of either direct damage to cells of the oral mucosa or indirect injury associated with concomitant myelosuppression. Cancer chemotherapeutic agents which are known to produce direct stomatotoxicity include methotrexate, doxorubicin, vinblastine and the like. Patients having had prior radiation complicated by mucositis are subject to a "recall" reaction, whereby mucositis is exacerbated by further treatment with doxorubicin.

Combination chemotherapy for transitional cell carcinoma consisting of methotrexate, vinblastine, doxorubicin and cisplatin, commonly referred to collectively as "M-VAC" is a regimen capable of inducing complete and partial responses in 69% of patients; however, mucositis, leukopenia and the ensuing complication of fever and infection are a frequent consequence of this treatment. Other complications associated with chemotherapy or radiation therapy include alopecia, nausea and vomiting.

Mucositis is a generic term associated with inflammation of the mucosal lining with or without ulceration as a result of direct damage to the cells of the oral mucosa or indirect injury associated with concomitant myelosuppression. Anti-neoplastic therapy includes the use of cancer chemotherapeutic agents which produce direct stomatotoxicity including but not limited to methotrexate, doxorubicin, vinblastine, bleomycin, vincristine and the like. Illustrative of various types of mucositis include oral stomatitis, digestive tract ulcerations, gingivitis, and mucocutaneous ulcerations. In addition, other potential diseases related to mucositis include diseases associated with ulceration of intestinal tract (i.e. ulcerative colitis, Crohns disease etc.), autoimmune disease(s), (Behcets syndrome) and the like. Mucositis is commonly induced as a result of anti-neoplastic therapy which includes, for example, the use of cancer chemotherapeutic agents which interfere with both normal and malignant cell replication by having a mode of action affecting cell division or metabolism. Chemotherapy is frequently employed to treat malignant disorders and provides a systemic means for reducing or preventing malignant cell proliferation.

Conventional therapy utilized in the systemic treatment of diagnosed mucositis includes palliative therapy, such as administration of local anesthetics, i.e. viscous xylocaine; pain medication such as codeine with acetaminophen; treatment with agents that coat the lining of the mouth, such as substrate of milk of magnesia; sodium bicarbonate, 3% hydrogen peroxide, and the like. In addition, leucovorin, (D, L, $N^5$-formyl tetrahydrofolic acid) has been used to prevent mucositis associated with methotrexate. Antifungal agents have been shown only to prevent or reduce secondary fungal infection resulting from already established mucositis. In addition, acyclovir treatment has been used to treat mucocutaneous herpes infections occurring in the setting of chemotherapy induced mucositis. Typically, a patient suffering the effects associated with mucositis will have to reduce the amount of chemotherapy and may suffer additional complications including, for example, pain, hemorrhage, reduced nutritional intake, secondary infections and the like.

Recently, granulocyte colony stimulating factors (GCSF), a hematopoietic glycoprotein which controls the proliferation of granulocytes in vitro and in vivo have been purified, molecularly cloned and expressed as a recombinant protein, Souza, et al., "Recombinant human granulocyte colony stimulating factor; effects on normal and leukemic myeloid cells", Science 1986; 232:61–65. Administration of recombinant human granulocyte colony stimulating factor (rhG-CSF), a specific growth and differentiation factor for neutrophil granulocytes in vitro id , and in vivo in normal cynomolgous primates Welte, K., et al. "Recombinant human granulocyte colony stimulating factor effects on hematopoiesis in normal and cyclophosphamide treated primates", Jour. Ep. Med. 1987; 165 941–948, has also been shown to shorten the period of neutropenia in cynomolgous primates treated with either high dose cyclophosphamide id. busulfan, Welte, K , et al. "In vivo effects of recombinant human GCSF in therapy induced neutropenias in primates", ISEH. 1987; 16:72 or autologous transplantation, Gillio, A. P., et al. "Effects of recombinant human granulocyte colony stimulating factor on hematopoiesis reconstitution following autologous bone marrow transplantation in primates, Transplant Proc. 1987; In Press.

SUMMARY OF THE INVENTION

This invention provides a method of preventing mucositis in a subject susceptible to mucositis comprising administering to the subject a prophylactically effective amount of granulocyte colony stimulating factor or a polypeptide analog thereof having substantially the same amino acid sequence and the activity of naturally occurring granulocyte colony stimulating factor. The analog may be a nonglycosylated polypeptide having an amino acid sequence identical to the sequence of the polypeptide component of naturally occurring granulocyte colony stimulating factor except for the presence of an additional methionine at the N-terminus. The granulocyte colony stimulating factor or the polypeptide analog thereof having substantially the same amino acid sequence and the activity of granulocyte colony stimulating factor may be produced in a foreign host by recombinant DNA techniques and is free of other polypeptides of human origin.

This invention further provides a method of treating mucositis in a subject having mucositis comprising administering to the subject a therapeutically effective amount of granulocyte colony stimulating factor or a polypeptide analog thereof having substantially the same amino acid sequence and the activity of naturally occurring granulocyte colony stimulating factor. The analog may be a nonglycosylated polypeptide having an amino acid sequence identical to the sequence of the polypeptide component of naturally occurring granulocyte colony stimulating factor except for the presence of an additional methionine at the N-terminus. The granulocyte colony stimulating factor or the polypeptide analog thereof having substantially the same amino acid sequence and the activity of granulocyte colony stimulating factor may be produced in a foreign host by recombinant DNA techniques and is free of other polypeptides of human origin.

The invention still further a composition for the prevention of mucositis comprising a prophylactically effective amount of granulocyte colony stimulating factor or a polypeptide analog thereof having substantially the same amino acid sequence and the activity of naturally occurring granulocyte colony stimulating factor and a pharmaceutically acceptable carrier.

Finally, this invention provides a composition for the treatment of mucositis comprising a therapeutically effective amount of granulocyte colony stimulating factor or a polypeptide analog thereof having substantially the same amino acid sequence and the activity of naturally occurring granulocyte colony stimulating factor and a pharmaceutically acceptable carrier.

DETAILED DESCRIPTION OF THE INVENTION

Figure 1:
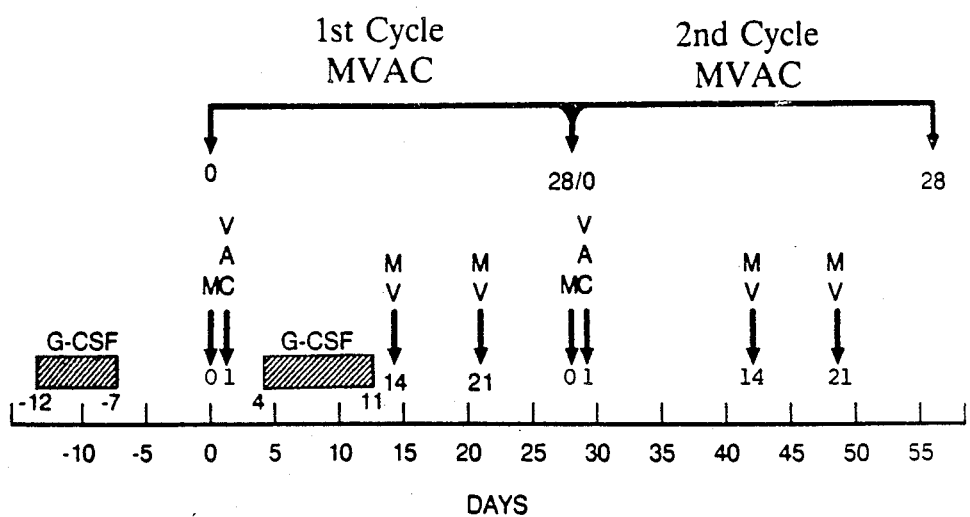
FIG. 1 describes a schematic of a M-VAC regimen utilizing recombinant hG-CSF.

This invention provides a method of preventing mucositis in subject susceptible to mucositis. This method comprises administering to the subject a prophylactically effective amount of granulocyte colony stimulating factor, e.g. purified naturally occurring granulocyte colony stimulating factor, or a polypeptide analog thereof having substantially the same amino acid sequence and the activity of naturally occurring granulocyte colony stimulating factor.

Typically, the method will be employed on a human patient who is susceptible to mucositis as a result of anti-neoplastic therapy, for example, chemotherapy or radiation therapy, and the administering will be effected in any of the various well known method for administering prophylactic drugs, such as intravenously, or subcutaneously. In the practices of the method of this invention prophylactically effective amounts, e.g. amounts from about 1 to about 100 $\rho$g/kg body weight/day, desirably from about 3 to about 60 $\mu$g/kg body weight/day are administered.

As used herein, the polypeptide analog means a polypeptide which has the activity of the naturally occurring polypeptide, but differs from it in at least one of the following ways:
(1) the presence of one or more additional amino acids at one or both termini of the polypeptide; or
(2) the presence of one or more different amino acids within the polypeptide; or
(3) the absence of acetylation or glycosylation.

In one embodiment, the polypeptide analog is a nonglycosylated polypeptide having an amino acid sequence identical to the sequence of the polypeptide component of naturally occurring granulocyte colony stimulating factor except for the presence of an additional methionine at the N-terminus.

As used herein, a foreign host is any host cell in which granulocyte colony stimulating factor does not naturally occur, including bacterial, yeast and mammalian cells, and recombinant DNA techniques are any of the well known techniques available to those skilled in the art for producing polypeptides in foreign host cells.

This invention also provides a method of treating mucositis in a subject having mucositis which comprises administering to the subject, e.g. a human patient, a therapeutically effective amount of granulocyte colony stimulating factor or a polypeptide analog thereof having substantially the same amino acid sequence and the activity of naturally occurring granulocyte colony stimulating factor. In this regard, a therapeutically effective amount is typically between about 1 and about 100, desirably between about 3 and about 60 $\mu$g/kg body weight/day. This invention is particularly useful for treating mucositis in human patents having mucositis as a result of anti-neoplastic therapy, e.g. chemotherapy or radiation therapy.

The method of this invention may be employed prior to, during, or subsequent to chemotherapy or radiation therapy and permit use of chemotherapeutic agents at higher doses or for more prolonged periods of time, or both.

Finally, this invention also provides composition for preventing mucositis and for treating mucositis comprising a prophylactically or therapeutically effective amount of granulocyte colony stimulating factor or a polypeptide analog thereof and a pharmaceutically acceptable carrier. Such amounts may be readily ascertained by one of ordinary skill in the art and may vary depending upon the particular individual being treated the severity of the condition, the administration regimen being followed, and the like. It has been found that administration of recombinantly produced granulocyte colony stimulating factor in a range from about 1–100, preferably from about 3–60 lg/kg body weight/day is effective in preventing or substantially reducing mucositis associated with epithelial cell damage chemotherapy.

The pharmaceutically acceptable carrier may be any of the carriers well known in the art. One such carrier is a buffered solution containing essentially no salt and a sufficient amount of mannitol and/or a non-ionic detergent such as Tween, to prevent aggregation.

Typical regimens for administration of the colony stimulating factors in accordance with the present invention to treat chemotherapy-induced mucositis include but are not limited to MACOP-B (lymphoma) and doxorubicin (breast) The specific regimen will depend upon the particular chemotherapeutic agent employed, chemotherapy regimen and the like.

Advantages provided by the methods of the present invention include prevention or reduction in the severity of chemotherapy and radiation therapy induced mucositis, reduction or prevention of secondary infection due to mucositis, increased nutritional intake; ease of swallowing, decrease in diarrhea, possible increase in chemotherapy or radiation therapy dosage and the like.

The following example will further illustrate the invention, although it will be understood that the invention is not limited to this specific embodiment

EXAMPLE 1

All patients with histologically-confirmed transitional cell carcinoma of the genitourinary tract, who exhibited a greater than two-fold increase in their absolute neutrophil count (ANC) on Days 5 and 6 of a pre-chemotherapy course of recombinant hG-CSF (first course). A study of human recombinant colony stimulating factor in patients with transitional cell carcinoma, were candidates to receive rhG-CSF (second course) during the first cycle of M-VAC chemotherapy (FIG. 1). Eighteen of the original twenty-two patients entered on to the first part of the study proved eligible to receive the second course of rhG-CSF. One patient received only one day of rhG-CSF and was therefore not eligible: the remaining three ineligible patients, treated at the 1 μg per kilogram per day dose level, had a less than two-fold increase in ANC on Days 5 and 6 of the first course of rhG-CSF.

Also included were patients who had not received prior rhG-CSF to be treated with rhG-CSF during their second cycle of M-VAC and not during their first. In addition, some patients who were eligible for the study, but chose not to participate, allowed their blood counts to be monitored during their first cycle of M-VAC. These two groups of patients served as control or 0 dose level rhG-CSF patients for the first cycle of M-VAC chemotherapy.

A complete blood count with white blood cell (WBC) differential and reticulocyte count was obtained daily or every other day through day 14 of the second cycle of M-VAC. In some instances, the blood count was monitored through Day 28 of the second cycle of M-VAC. Liver and renal function tests, electrolytes, urinalysis and leukocyte alkaline phospatase were obtained prior to chemotherapy and repeated weekly for the remainder of the study.

The rhG-CSF used in these studies was produced by E. coli through recombinant DNA techniques Souza, et al., ibid. The rhG-CSF is 95% or more pure, is formulated in an aqueous buffer and has no measurable endotoxin as detected by the limulus amebocyte assay. The specific activity of the recombinant protein is $1 \times 10^8$ or more units per milligram of protein.

The rhG-CSF was diluted in 50 cc of D5W containing 2 mg/ml HSA and administered once daily as a half-hour intravenous infusion. The first course of treatment prior to chemotherapy consisted of daily administration of rhG-CSF at dose levels of 1, 3, 10, 30 and 60 μg per kilogram of body weight per day for a total of six days or until the WBC count reached 100,000/mm$^3$. Patients were then eligible to receive a second course of rhG-CSF following the initial doses of M-VAC in the first cycle of chemotherapy (FIG. 1). Dose levels in this portion of the study included 3, 10, 30 and 60 μg per kilogram of body weight per day.

The schedule of M-VAC chemotherapy for transitional cell carcinoma consists of methotrexate, 30 mg per square meter on Day 0; doxorubicin, 30 μg per square meter; vinblastine, 3 mg per square meter; and cisplatin, 70 mg per square meter on Day 1. The same dose of methotrexate and vinblastine were then administered again on Day 14 and Day 21 of the cycle. The regimen is then recycled on Day 28. In this example, rhG-CSF was administered on Day 4 through Day 11 during the first cycle of M-VAC only (FIG. 1). In this way, it was possible to compare the following parameters: (1) the ANC profile for Day 0 through Day 14, (2) the incidence and duration of neutropenia, (3) the incidence of neutropenia on Day 14 and (4) the ability to receive Day 14 chemotherapy on schedule, within patients in which rhG-CSF was administered in their first M-VAC cycle, but not in their second M-VAC cycle. In the first cycle of M-VAC, it was possible also to evaluate these parameters in patients receiving chemotherapy only and compare them to patients treated with chemotherapy plus rhG-CSF.

The clinical characteristics of the study group are shown in Table 1. Twenty-four patients were analyzed Eighteen patients received treatment with rhG-CSF during their first and not during their second cycle of M-VAC. In this group four patients had received prior pelvic radiation therapy, and one prior systemic chemotherapy and three prior intravesical chemotherapy. Six additional patients had their blood counts monitored, but received no recombinant hG-CSF during their furst cycle of M-VAC.

TABLE 1

| Patient Profile of Those Patients Qualifying for the Second Course of rhG-CSF | |
|---|---|
| Number of Patients Entered For: | |
| Cycle 1 w/G-CSF | 18 |
| Cycle 1 w/o G-CSF | 6 |
| Median Age (years) | 59 (41–77) |
| Male:Female | 19:5 |
| Median Performance Status | 85 (65–100) |
| Prior Therapy: | |
| Systemic Chemotherapy | 2 |
| Intravesical Chemotherapy | 3 |
| Radiation Therapy[1] | 5 |
| IL-2 plus LAK[2] | 1 |
| Number of Patient Evaluable For: | |
| ANC Profiles Cycle 1 | 23 |
| ANC Profiles Cycle 2 | 16[3] |
| Day 14 ANC Cycle 1 | 24 |
| Day 14 ANC Cycle 2 | 17[3] |

[1]Whole pelvic RT
[2]Lymphocyte Activated Killer Cells
[3]Only cycle 1 G-CSF patients were evaluable for cycle 2

TABLE 2

| | | | Number of patients with mucositis graded according to the WHO classification. | | | | |
|---|---|---|---|---|---|---|---|
| MVAC | | | | | Grade | | |
| Cycle | # Patients | G-CSF | 0 | 1 | 2 | 3 | 4 |
| 1 | 6 | — | 3 | 1(27)[1] | 1(13) | 1(25) | 0 |
| 1[2] | 18 | + | 16 | 0 | 2(6,19) | 0 | 0 |

TABLE 2-continued

| MVAC Cycle | # Patients | G-CSF | Number of patients with mucositis graded according to the WHO classification. Grade | | | | |
|---|---|---|---|---|---|---|---|
| | | | 0 | 1 | 2 | 3 | 4 |
| $2^2$ | 18 | — | 10 | 0 | 3(10,18,22) | 4(5,6,12,19) | 1(21) |

[1]Number in parentheses refer to the patients indentity number.
[2]P = 0.041 by the McNemer's test, comparing the proportion of patients, not exhibiting mucositis in C1 (w/rhG-CSF) verses C2 (w/o rhG-CSF).

Prior therapy for this group of patients consisted of systemic chemotherapy and treatment both radiation and Interleukin-2 plus lymphocyte activated killer cells Pizzo, et al., ibid. No significant difference in the mean age, performance status, creatinine clearance, baseline WBC or ANC was noted for rhG-CSF treated and non-treated patients. Stages of transitional cell carcinoma for this group included seven T2N0, six T3N0, one T3N2, one T3N4, one T4N0 and eight M1.

The incidence of mucositis in the first fourteen days of the first and second cycles of M-VAC was assessed in patients receiving and not receiving rhG-CSF (Table 2). The extent of mucositis was graded according to the WHO classification as follows: grade 1—soreness and erythema of oral mucosa; grade 2—erythema, ulcerations, able to eat solid food; grade 3—ulcerations requiring liquid diet only, grade 4—ulcerations, alimentation not possible. Only two out of eighteen patients (11%) developed grade 2 mucositis when rhG-CSF was administered in the first cycle of M-VAC. In each of these two cases, grade 2 mucositis consisted of only one small ulceration. In the second cycle, when M-VAC was given without rhG-CSF treatment, eight of the same 18 patients (44%) developed grade 2-4 oral complications. Furthermore, three of six (50%) of these patients treated with M-VAC alone in the first cycle developed grade 1-3 stomatitis, respectively. It has been reported that M-VAC is associated with a forty percent incidence of mucositis, Sternberg, et al., "Preliminary results of M-VAC (Methotrexate, Vinblastine, Doxorubicin and Cisplatin) for transitional cell carcinoma of the urothelium", J. Urol. 1985; 133:403-407. As illustrated in the above Example, during Day 0-14, only 11% of patients developed minimal grade 2 mucositis when they were treated with rhG-CSF in the first cycle of M-VAC. This was in marked contrast to 50% (grade 1-3) and 44% (grade 2-4) of patients not receiving rhG-CSF in their first or in their second cycle of chemotherapy, respectively. The method of the present invention enables one to either prevent the occurrence and/or severity of mucositis and to accelerate recovery from mucositis (grade 1-4, WHO classification).

Oral ulcerations are known to be a frequent complication of primary neutropenic disorders including cyclic neutropenia, Kostmann,s syndrome and idiopathic neutropenia. The major function of neutrophil granulocytes is to prevent or retard the infiltration of infectious agents. All mucosal linings represent the major structural protective barrier for the mucosa host against foreign pathogens. Mature neutrophils in the process of being lost through all epithelial surfaces are likely to be continually involved in the phagocytosis of potential pathogens as part of primary host defense. Naturally occurring G-CSF and recombinant hG-CSF have been shown to enhance Fc receptors and formyl peptide receptors on neutrophils. Therefore, recombinant hG-CSF may reduce the incidence of mucositis by enhancing the number of neutrophils, as well as their functional capability to guard the mucosal barriers more efficiently. Thus, the decreased incidence of mucositis in patients treated with rhG-CSF may be in part explained by the decrease noted in iatrogenically-induced neutropenia. Recombinant hG-CSF may also have some additional effect on the integrity of epithelium since some patients (#12, 22 and 25) with neutrophil counts of 1500 or more per microliter developed mucositis when they were not receiving rhG-CSF. In addition, the direct injury of Adriamycin, Methotrexate and Vinblastine on oral and intestinal epithelium is well established and independent of their myelosuppressive toxicity.

A positive correlation exists between dose and response for anti-tumor agents Blum, et al. Principles of dose, schedule and combination chemotherapy. In: Cancer Medicine, Holland J, Frei E III, eds. Lea and Febiger, Philadelphia, 1982; 730-751, however, the evidence that further intensification of chemotherapy increases response rates remains controversial. The doses of chemotherapeutic drugs used in combination chemotherapy for non-hematopoietic tumors are limited by what investigators consider to be acceptable degrees of hematological and gastrointestinal toxicity, as well as numbers of admissions to the hospital for fever in the setting of neutropenia. The ability to diminish the aforementioned side effects of chemotherapy has important ramifications with regard to the definition of maximum tolerated dose. The use of recombinant hG-CSF in conjunction with both established and new cancer drugs should alter their profile of dose limiting toxicity. This will enable investigators for the first time to test the hypothesis that larger doses of anti-neoplastic drugs are more beneficial in the treatment of cancer.

Various other examples and modifications of the foregoing description will be apparent to a person skilled in the art without departing from the spirit and scope of the invention, and it is intended that all such examples and modifications be included within the scope of the appended claims.

What is claimed is:

1. A method of preventing mucositis in a subject susceptible to mucositis comprising administering to the subject a prophylactically effective amount of granulocyte colony stimulating factor or a polypeptide analog thereof having substantially the same amino acid sequence and the activity of naturally occurring granulocyte colony stimulating factor.

2. A method of claim 1, wherein the analog is a non-glycosylated polypeptide having an amino acid sequence identical to the sequence of the polypeptide component of naturally occurring granulocyte colony stimulating factor except for the presence of an additional methionine at the N-terminus.

3. A method of claim 1, wherein the granulocyte colony stimulating factor or the polypeptide analog thereof having substantially the same amino acid sequence and the activity of granulocyte colony stimulating factor is produced in a foreign host by recombinant DNA techniques and is free of other polypeptides of human origin.

4. A method of claim 1, wherein the granulocyte colony stimulating factor is the purified naturally occurring polypeptide.

5. A method of claim 1, wherein the subject is a human patient.

6. A method of claim 1, wherein the subject is susceptible to mucositis as a result of anti-neoplastic therapy.

7. A method of claim 6, wherein the anti-neoplastic therapy is chemotherapy.

8. A method of claim 6, wherein the anti-neoplastic therapy is radiation therapy.

9. A method of claim 1, wherein the prophylactically effective amount is between about 1 and about 100 μg/kg body weight/day.

10. A method of claim 9, wherein the prophylactically effective amount is between about 3 and about 60 μg/kg body weight/day.

11. A method of treating mucositis in a subject having mucositis comprising administering to the subject a therapeutically effective amount of granulocyte colony stimulating factor or a polypeptide analog thereof having substantially the same amino acid sequence and the activity of naturally occurring granulocyte colony stimulating factor.

12. A method of claim 11, wherein the analog is a nonglycosylated polypeptide having an amino acid sequence identical to the sequence of the polypeptide component of naturally occurring granulocyte colony stimulating factor except for the presence of an additional methionine at the N-terminus.

13. A method of claim 11, wherein the granulocyte colony stimulating factor or the polypeptide analog thereof having substantially the same amino acid sequence and the activity of granulocyte colony stimulating factor is produced in a foreign host by recombinant DNA techniques and is free of other polypeptides of human origin.

14. A method of claim wherein the granulocyte colony stimulating factor is the purified naturally occurring polypeptide.

15. A method of claim 11, wherein the subject is a human patient.

16. A method of claim 11, wherein the subject has mucositis as a result of anti-neoplastic therapy.

17. A method of claim 16, wherein the anti-neoplastic therapy is chemotherapy.

18. A method of claim 16, wherein the anti-neoplastic therapy is radiation therapy.

19. A method of claim 11, wherein the therapeutically effective amount is between about 1 and about 100 μg/kg body weight/day.

20. A method of claim 19, wherein the therapeutically effective amount is between about 3 and about 60 μg/kg body weight/day.

* * * * *